United States Patent [19]

Huo

[11] Patent Number: 5,922,535
[45] Date of Patent: Jul. 13, 1999

[54] IDENTIFYING SEQUENCE DIFFERENCES IN NUCLEIC ACID POPULATIONS

[76] Inventor: Li Huo, 73 Fifth St., Apt. 1, Cambridge, Mass. 02141

[21] Appl. No.: 08/553,185

[22] Filed: Nov. 7, 1995

[51] Int. Cl.⁶ .............................. C12Q 1/68; C07H 21/02; C07H 21/04
[52] U.S. Cl. .............................. 435/6; 536/23.1; 536/24.3
[58] Field of Search ................................ 435/6; 536/23.1, 536/24.3

[56] References Cited

U.S. PATENT DOCUMENTS

| | | | |
|---|---|---|---|
| 4,946,773 | 8/1990 | Maniatis et al. | 435/6 |
| 5,011,769 | 4/1991 | Duck et al. | 435/6 |
| 5,217,863 | 6/1993 | Cotton et al. | 435/6 |
| 5,403,711 | 4/1995 | Walder | 435/6 |

FOREIGN PATENT DOCUMENTS

WO 9320233 A1 10/1993 WIPO.

OTHER PUBLICATIONS

Lu et al., Genomics 14:249–255 (1992).
Hsu et al., Carcinogenesis 15(8): 1657–1662 (1994).
Matthews et al., Analytical Biochemistry 169: 1–25 (1988).
Bidichandani et al., Hum. Genetics 95:531–538 (1995).
Forrest et al., Am. J. Hum. Genetics 49:175–183 (1991).
Akli et al., Genomics 11: 124–134 (1991).
Bateman et al., Biochem. J. 276: 765–770 (1991).
Purandare et al., Hum. Molecular Genetics 3(7):1109–1115 (1994).
Bugg et al., PNAS 88:7654–7658 (1991).
Cotton et al., "Reactivity of cytosine and thymine in single–base–pair mismatches with hydroxylamine and osmium tetroxide and its application to the study of mutations", Proc. Natl. Acad. Sci. USA, vol. 85, pp. 4397–4401, Jun. 1988.
Myers et al., "Detection of single base substitutions in total genomic DNA", Nature, vol. 313, pp. 495–497, 1985.
Myers et al., "Detection of single base substitutions by ribonuclease cleavage at mismatches in RNA:DNA duplexes", Science, vol. 230, pp. 1242–1246, Dec. 13, 1985.
Orita et al., "Detection of polymorphisms of human DNA by gel electrophoresis as single–strand conformation polymorphisms", Proc. Natl. Acad. Sci. USA, vol. 86, pp. 2766–2770, Apr. 1989.
Shenk et al., "Biochemical method for mapping mutational alterations in DNA with S1 nuclease: the location of deletions and temperature–sensitive mutations in simian virus 40", Proc. Nat. Acad. Sci. USA, vol. 72, No. 3, pp. 989–993, Mar. 1975.

*Primary Examiner*—W. Gary Jones
*Assistant Examiner*—Ethan Whisenant
*Attorney, Agent, or Firm*—Choate, Hall & Stewart

[57] ABSTRACT

Methods of identifying sequence differences between or among nucleic acid populations are described. Nucleic acid strands from different populations are hybridized with one another so that mismatch-containing duplexes are formed. Mismatch-containing duplexes are cleaved in a mismatch-dependent fashion and cleavage products are isolated and used to identify the genetic sequences that differ in the nucleic acid populations.

4 Claims, 3 Drawing Sheets further characterization of the DNA fragments

```
                        SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 8 base pairs
          (B) TYPE: nucleic acid
          (C) STRANDEDNESS: Not Relevant
          (D) TOPOLOGY: Not Relevant (ii) MOLECULE TYPE: other nucleic acid
          (A) DESCRIPTION: /desc = "DNA"

(vii) IMMEDIATE SOURCE:
          (B) CLONE: NotI site (xi) SEQUENCE DESCRIPTION: SEQ ID NO:1:

GCGGCCGC                                                              8

(2) INFORMATION FOR SEQ ID NO:2:

(i) SEQUENCE CHARACTERISTICS:
          (A) LENGTH: 6 base pairs
          (B) TYPE: nucleic acid
          (C) STRANDEDNESS: Not Relevant
          (D) TOPOLOGY: Not Relevant (ii) MOLECULE TYPE: other nucleic acid
          (A) DESCRIPTION: /desc = "DNA"

(vii) IMMEDIATE SOURCE:
          (B) CLONE: XhoI site (xi) SEQUENCE DESCRIPTION: SEQ ID NO:2:

CTCGAG                                                                6

(2) INFORMATION FOR SEQ ID NO:3:

(i) SEQUENCE CHARACTERISTICS:
          (A) LENGTH: 6 base pairs
          (B) TYPE: nucleic acid
          (C) STRANDEDNESS: Not Relevant
          (D) TOPOLOGY: Not Relevant
```

(ii) MOLECULE TYPE: other nucleic acid
            (A) DESCRIPTION: /desc = "DNA"

(vii) IMMEDIATE SOURCE:
            (B) CLONE: EcoRI site (xi) SEQUENCE DESCRIPTION: SEQ ID NO:3:

GAATTC                                                                          6

(2) INFORMATION FOR SEQ ID NO:4:

(i) SEQUENCE CHARACTERISTICS:
            (A) LENGTH: 6 base pairs
            (B) TYPE: nucleic acid
            (C) STRANDEDNESS: Not Relevant
            (D) TOPOLOGY: Not Relevant (ii) MOLECULE TYPE: other nucleic acid
            (A) DESCRIPTION: /desc = "DNA"

(vii) IMMEDIATE SOURCE:
            (B) CLONE: sequence A (xi) SEQUENCE DESCRIPTION: SEQ ID NO:4:

GAAATC                                                                          6

(2) INFORMATION FOR SEQ ID NO:5:

(i) SEQUENCE CHARACTERISTICS:
            (A) LENGTH: 6 base pairs
            (B) TYPE: nucleic acid
            (C) STRANDEDNESS: Not Relevant
            (D) TOPOLOGY: Not Relevant (ii) MOLECULE TYPE: other nucleic acid
            (A) DESCRIPTION: /desc = "DNA"

(vii) IMMEDIATE SOURCE:
            (B) CLONE: sequence B (xi) SEQUENCE DESCRIPTION: SEQ ID NO:5:

GAAGTC                                                                          6

(2) INFORMATION FOR SEQ ID NO:6:

(i) SEQUENCE CHARACTERISTICS:
            (A) LENGTH: 34 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "DNA"

(vii) IMMEDIATE SOURCE:
            (B) CLONE: Example 1 primer for first strand cDNA
                synthesis (xi) SEQUENCE DESCRIPTION: SEQ ID NO:6:

ATAAGAATGC GGCCGCTTTT TTTTTTTTTT TTTT                                           34

(2) INFORMATION FOR SEQ ID NO:7:

(i) SEQUENCE CHARACTERISTICS:
            (A) LENGTH: 10 base pairs
            (B) TYPE: nucleic acid
            (C) STRANDEDNESS: Not Relevant
            (D) TOPOLOGY: Not Relevant (ii) MOLECULE TYPE: other nucleic acid
            (A) DESCRIPTION: /desc = "DNA"

(vii) IMMEDIATE SOURCE:
    (B) CLONE: SalI linker (xi) SEQUENCE DESCRIPTION: SEQ ID NO:7:

CGGTCGACCG                                                                10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "DNA"

(vii) IMMEDIATE SOURCE:
        (B) CLONE: EcoRI linker (xi) SEQUENCE DESCRIPTION: SEQ ID NO:8:

CGGAATTCCG                                                                10

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA"

(vii) IMMEDIATE SOURCE:
        (B) CLONE: first strand of PvuII/EcoRI adapter (xi) SEQUENCE DESCRIPTION: SEQ ID NO:9:

CCAGCTGCG                                                                  9

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA"

(vii) IMMEDIATE SOURCE:
        (B) CLONE: second strand of PvuII/EcoRI adapter (xi) SEQUENCE DESCRIPTION: SEQ ID NO:10:

AATTCGCAGC TGG                                                            13

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "DNA"

(vii) IMMEDIATE SOURCE:
        (B) CLONE: SalI linker (xi) SEQUENCE DESCRIPTION: SEQ ID NO:11:

CGGTCGACCG                                                                 10

IDENTIFYING SEQUENCE DIFFERENCES IN NUCLEIC ACID POPULATIONS

BACKGROUND OF THE INVENTION

Alterations in nucleotide sequences can have profound effects on cells. For example, many tumors and many genetic diseases result from alteration, or mutation, of particular nucleotide sequences. Mutations in nucleotide sequences that encode proteins can result in production of proteins with altered polypeptide sequences and, in some instances, altered biological activities. Changes in the activity of a single protein can sometimes have profound effects on the physiology of an entire organism.

In order to develop effective preventive, diagnostic and therapeutic methods for treatment of cancer and hereditary diseases, we must first identify the genetic mutations that contribute to disease development. Typically, mutations are identified in studies of cloned genes whose normal sequences are already known (see, for example, Suzanne et al., *Science* 244:217, 1989; Kerem et al., *Science* 245:1073, 1989). That is, a gene is first identified as being associated with a disorder, and particular sequence changes that correlate with the diseased state are subsequently identified.

A variety of techniques have been used to identify sequence variations in nucleic acids. For example, Restriction Fragment Length Polymorphism (RFLP) analysis detects restriction sites generated by mutations or alterations in nucleotide sequences (see Kan et al., *Lancet* ii:910, 1978); Denaturing Gradient Gel Electrophoresis and Single Stranded DNA Electrophoretic Mobility Studies identify nucleotide sequence differences through alterations in the mobility of bands in electrophoresis gels (see Myers et al., *Nature* 313:495, 1985; Orita et al., *Proc. Natl. Acad. Sci. USA* 86:2766, 1989); Chemical Cleavage analysis identifies mismatched sites in heteroduplex DNA (see Cotton, *Proc. Natl. Acad. Sci. USA* 85:4397, 1988); and RNase Cleavage analysis identifies mismatched sites in RNA-DNA or RNA-RNA heteroduplexes (see Myers et al., *Science* 230:1242, 1985; Maniatis et al. U.S. Pat. No. 4,946,773).

A significant problem with each of the above-described methods for identifying nucleic acid sequence differences is that prior knowledge of the gene of interest is generally required. Additionally, each of these methods utilizes DNA display techniques that limit the number of different genes that can be analyzed at one time. There is a need for development of techniques that allow identification of sequence alterations and mutations without prior knowledge of which gene has been disrupted. There is also a need for the development of techniques that allow analysis of multiple different sequence alterations at the same time.

SUMMARY OF THE INVENTION

The present invention provides a general method for the detection of sequence differences between two or more nucleic acid populations. The invention provides tools that can be used, for example, to identify polymorphisms in genomic DNA, to identify genetic mutations associated with disease states, and/or to identify genes whose primary transcripts are alternatively spliced.

Nucleotide sequence alterations can take the form of substitutions, deletions, additions, or rearrangements. When a strand of nucleic acid (e.g., a single strand of RNA or DNA) having an altered sequence is hybridized with a complementary sequence that has not been analogously altered, the heteroduplex will contain a mismatch, or an unpaired loop. Such mismatches or hairpin loops are susceptible to cleavage by various chemical and/or enzymatic agents.

The present invention encompasses the recognition that hybridization and mismatch cleavage techniques can be utilized to identify differences between nucleic acid populations. Specifically, according to the present invention, nucleic acid strands present in or produced from a first population are hybridized with complementary strands present in or produced from a second population. Mismatches are cleaved, and products of mismatched cleavage reactions are isolated. The isolated cleavage products are subsequently used to identify those sequences that differed between the two nucleic acid populations.

One of the advantages provided by the present invention is that it allows rapid identification of many different sequence alterations at the same time. That is, most conventional mutation discovery techniques identify one mutation in one gene. By contrast, the methods and system of the present invention allow analysis of multiple genes at the same time. Over 10,000 genes can be processed simultaneously in the procedures according to the present invention.

Additionally, as discussed above, the present invention allows identification of sequence differences in genes without any prior knowledge that the particular gene is relevant to the state (e.g., disease state, developmental stage, state of speciation, etc.) being studied. In fact, the present invention allows the identification of the relevant gene or genes by identification of those genes whose sequences are different in different nucleic acid populations.

The present invention therefore provides a method for identifying sequence differences in nucleic acid populations, the method comprising steps of (i) providing a first nucleic acid population; (ii) providing a second nucleic acid population having at least one difference in nucleotide sequence as compared with the first nucleic acid population; (iii) forming heteroduplexes between nucleic acid strands in the first and second nucleic acid populations, at least one of the heteroduplexes having a mismatch due to the at least one difference in nucleotide sequence; (iv) cleaving the at least one mismatched heteroduplex in a mismatch-dependent manner; and (v) isolating cleavage products.

The present invention also provides a method of identifying a gene whose nucleotide sequence is altered in different cells, the method comprising steps of (i) providing a first nucleic acid population from a first cell in which the gene has a first nucleotide sequence; (ii) providing a second nucleic acid population from a second cell in which the gene has a second nucleotide sequence that differs from the first nucleotide sequence in that at least one nucleotide has been substituted, added, deleted, or rearranged; (iii) forming heteroduplexes between nucleic acid strands in the first and second nucleic acid populations, at least one of the heteroduplexes having a mismatch due to the at least one difference in nucleotide sequence; (iv) cleaving the at least one mismatched heteroduplex in a mismatch-dependent manner; (v) isolating at least one cleavage product; and (vi) using the at least one isolated cleavage product to identify the gene whose nucleotide sequence was altered in the second cell as compared with the first cell.

The present invention further provides a method of identifying a gene whose transcript is alternatively spliced, the method comprising steps of (i) providing an RNA sample from a cell; (ii) producing a double-stranded DNA population from the isolated RNA; (iii) exposing said double-stranded DNA population to denaturing conditions; (iv) exposing the denatured DNA to annealing conditions so that heteroduplex double-stranded DNAs are formed, at least one heteroduplex double-stranded DNA consisting of a first strand corresponding to a first alternatively spliced transcript of a gene and a second strand corresponding to a second alternatively spliced transcript of the same gene, the at least one heteroduplex double-stranded DNA containing an unpaired region; (v) cleaving the at least one heteroduplex containing an unpaired region at said unpaired region; (vi) isolating at least one cleavage product; and (vii) using the at least one isolated cleavage product to identify the gene whose transcript was alternatively spliced.

Various aspects and implications of the present invention will be more fully understood with reference to the following Description of Preferred Embodiments, which should be read in light of the accompanying drawings.

DEFINITIONS

The term "cleavage", as used herein, refers to the breakage of a chemical bond between atoms or chemical groups. Cleavages can occur spontaneously or can be catalyzed, for example by small molecules, ions, radicals, or enzymes.

The term "isolated", as used herein, means separated from at least some of the components with which it is naturally associated. For example, a purified or partially-purified protein or nucleic acid is considered to be "isolated". The term "isolated" is intended to encompass molecules that are chemically equivalent to naturally-occurring molecules but that were produced in a manner other than the manner by which the equivalent molecules are produced in nature (e.g., that were produced in vitro, for example, by chemical synthesis or, in the case of DNA, by the polymerase chain reaction). The term "isolated" is also intended to encompass molecules that are chemically distinct from naturally-occurring molecules (e.g., that differ from a naturally-occurring molecule by the presence or absence of at least one covalent interaction).

The term "gene", as used herein, refers to a portion of a DNA molecule that is expressed in cells. The term is intended to encompass both protein-coding sequences and sequences that produce function RNAs.

The term "mutation" refers to a structural change in the nucleotide sequence of a nucleic acid molecule. Preferably, the term refers to a change that is a deviation from a "normal" (i.e., wild-type) sequence, but, because the present invention relates to sequence comparisons between or among nucleic acids whose "normal" sequence may not be known, the term "mutation" is often used in its broadest sense, in a comparative context, to mean a difference in nucleotide sequence between two corresponding nucleic acid samples.

DESCRIPTION OF PREFERRED EMBODIMENTS

As discussed above, the present invention provides a general method for the detection of sequence differences between or among nucleic acid populations. The method of the present invention can be utilized in comparisons of RNA populations with one another, of DNA populations with one another, and/or of RNA populations with DNA populations. The only requirement is that the nucleic acid populations to be compared must be capable of hybridizing with one another, or of being converted into a form capable of hybridizing, so that at least one mismatch-containing heteroduplex is produced. Once the mismatch-containing heteroduplex is formed, any available mismatch-dependent cleavage agent is used to cut the heteroduplex, preferably at or near the mismatch site, and appropriate cleavage products are isolated for subsequent use, for example as probes.

Figure 1:
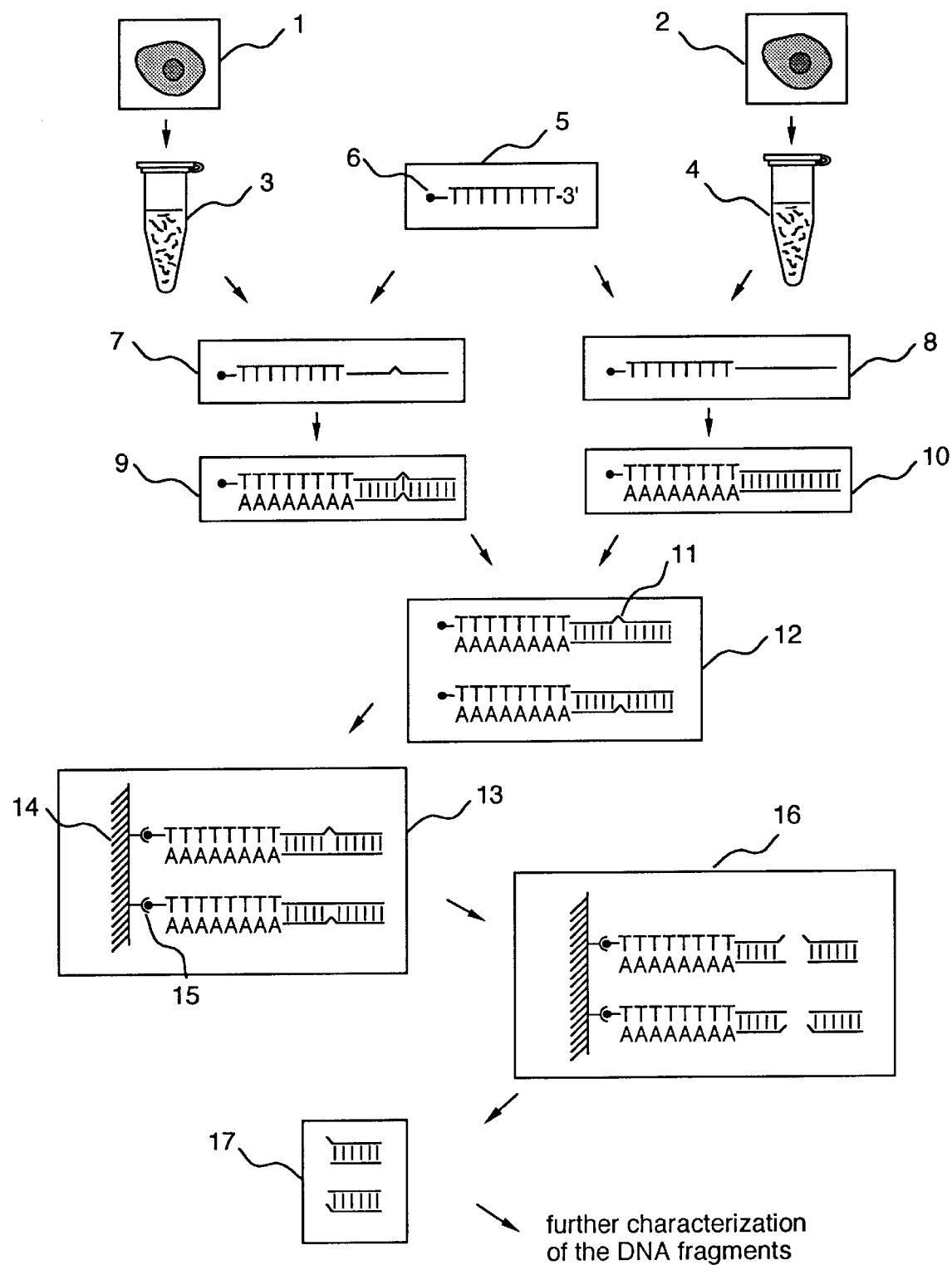
FIG. 1 is a schematic representation of a method according to the present invention for identifying sequence alterations in populations of mRNA.

Below, we discuss individual applications of the present invention in order to more fully illustrate its performance.
Detecting Sequence Differences in mRNA Populations FIG. 1 presents a schematic representation of a method for detecting mismatches in mRNA populations according to the present invention. Specifically, FIG. 1 shows a first cell 1 and a second cell 2 from which poly-A messenger RNA (mRNA) is isolated according to known techniques (see, for example, Sambrook et al. *Molecular Cloning: A Laboratory Manual* Cold Spring Harbor Press, Cold Spring Harbor, N.Y., 1989, Chapter 7; Gilman et al. *Current Protocols in Molecular Biology*, Ausubel et al., eds, John Wiley & Sons, New York, N.Y., 1994, Chapter 4; Xie et al. *Biotechniques* 11:324, 1991; Walther et al. *Nuc. Acids Res.* 21:1682, 1993; Aviv et al. *Proc. Nati. Acad. Sci. USA* 69:1408, 1972, each of which is hereby incorporated by reference; see also poly-A mRNA isolation kits and associated materials from, for example, Pharmacia Biotech, Piscataway N.J., 1995 catalog #27-9255-01 and #27-9254-01; Stratagene, La Jolla, Calif. 1995 catalog #200347, #200345, #200348, #200349, and #200344).

The first and second cells 1 and 2 depicted in FIG. 1 differ from one another in that the first cell 1 has at least one mutation in a protein-coding gene as compared with the second cell 2, so that the first mRNA population 3 isolated from the first cell 1 has at least one sequence alteration relative to the second mRNA population 4 isolated from the second cell 2.

As will be apparent to one of ordinary skill in the art, the desirable degree of relatedness of the first 1 and second 2 cells to one another will depend somewhat on the goal of the investigator utilizing the technique. For example, if one is interested in identifying a gene that, when mutated, contributes to disease development, it is generally desirable to use cells as closely related as possible so that the disease-causing mutation is likely to be the only sequence difference between the cells, or one of only a few sequence differences. In such cases, it is preferable to use two different cells (i.e. one diseased cell and one normal cell) from the same individual, and desirably from the same tissue within that individual. Of course, it is understood that often more than one mutation contributes to the development of a diseased state, and that additional mutations are often accumulated during progression of a disease, so that even closely-related cells may have many sequence differences when one is a diseased cell and one is normal.

On the other hand, it may be desirable in some applications of the present invention to identify any and all differences between two particular cells, even though the cells are not highly related to one another. As will be readily apparent to one of ordinary skill in the art, any two cells can be compared to one another using the techniques of the present invention. However, product analysis becomes more complicated when cells with multiple sequence differences are utilized.

Generally, it is desirable to run experimental reactions side-by-side with control reactions, for example, in which nucleic acids isolated from only the first 1 or only the second 2 cell are reacted with themselves. This procedure will define the "background" for the experimental reaction, which background results, for example, from formation of heteroduplexes containing different alleles of the same gene.

As shown in FIG. 1, first and second mRNA populations 3, 4, isolated from the first and second cells 1, 2, respectively, are copied into complementary DNA (cDNA) according to standard techniques (see, for example Sambrook et al. supra, Chapter 8; Klickstein et al. *Current Protocols in Molecular Biology*, Ausubel et al., eds, John Wiley & Sons, New York, N.Y., 1995, pp 5.5.1–5.5.14, each of which is incorporated herein by reference). Typically, a reverse transcriptase such as that from Moloney Murine Leukemia Virus (MMLV) is used in the reverse transcription reaction. As a result of this reverse transcription, first 9 and second 10 nucleic acid populations are produced from first 3 and second 4 mRNA populations, respectively.

In the particular embodiment presented in FIG. 1, a biotinylated poly-T primer 5 is used to promote synthesis of the cDNA strands 7, 8 complementary to the mRNA populations 3, 4. Any position, or in fact more than one position, on the primer can be biotinylated. Only 8 T residues are depicted in the biotinylated primer 5 in FIG. 1, but this is primarily for purposes of clarity. One of ordinary skill in the art would readily understand that primers approximately 16–20 nucleotides in length are preferred, and that in some cases it may be desirable to anchor the primers at the 5' end of the poly-A tail by including one or more non-T residues (e.g., dA, dC, dG, dAA, dAC, dAG, dAT, dCA, dCC, dCG, dCT, dGA, dGC, dGG, or dGT at the 3' end of the primer (see, for example, U.S. Pat. No. 5,262,311; Liang et al., *Science* 257:967, 1992; Kahn et al., *Nuc. Acids Res.* 19:1715, 1991, each of which is hereby incorporated by reference). Use of anchoring residues allows each primer to bind to, and direct reverse transcription from, only a subset of mRNA molecules in the first 3 and second 4 mRNA populations (see U.S. Pat. No. 5,262,311; Liang et al., supra).

It will be understood by one of ordinary skill in the art that a poly-T primer 5 is utilized in the embodiment of the invention depicted in FIG. 1 because use of such a primer allows analysis of substantially any mRNA with a poly-A tail. In some cases, it may be desirable to add poly-A tails to isolated RNAs, in order to allow analysis of RNAs that do not naturally contain such tails. Procedures for poly-A tail addition are known in the art, and commercial kits are available from a variety of sources (see, for example, Thompson et al. *BioTechniques* 19:416, 1995; Tabor *Current Protocols in Molecular Biology*, Ausubel et al., eds, John Wiley & Sons, New York, N.Y. 1987, pp 3.9.1–3.9.2, each of which is hereby incorporated by reference; see also poly-A addition kits and associated materials from, for example, Gibco BRL, Grand Island, N.Y., 1995 catalog #18032-011 and #18032-029; Amersham Life Sciences, Arlington Heights, Ill., 1995 catalog #E2180Y, #E74225Y, and #E74225Z).

Rather than, or in addition to, adding poly-A tails to isolated RNAs, it may be desirable, prior to the above-discussed reverse transcription step, to isolate poly-A-containing RNAs from the RNA populations 3, 4 isolated from cells 1 and 2. Techniques for isolating poly-A-containing RNAs are readily available in the art (see, for example, Aviv et al. *Proc. Natl. Acad. Sci. USA* 69:1408, 1972, incorporated herein by reference), and kits designed to simplify the procedures can be purchased from a variety of vendors (such as, for example, Pharmacia Biotech, Piscataway, N.J., 1995 catalog #27-9258-01 and #27-9254-01; Stratagene, La Jolla, Calif., 1995 catalog #200347, #200348, and #200349).

The reverse transcription step discussed above produces first 9 and second 10 nucleic acid populations consisting of cDNA/mRNA duplexes. It will typically be desirable, although not strictly necessary, to convert these hybrids into DNA duplexes, so that the first 9 and second 10 nucleic acid populations are converted to double stranded DNA populations. A variety of techniques, such as self-priming, replacement synthesis, and PCR, are available to convert cDNA/mRNA duplexes into double stranded DNA. Self-priming (see Sambrook et al., supra, pp 8.14, incorporated herein by reference) and replacement synthesis (see Sambrook et al., supra, pp. 8.15; Klickstein et al. *Current Protocols in Molecular Biology*, supra, 1995, pp. 5.5.1–5.5.14, each of which is incorporated herein by reference) are the preferred methods because they allow production of high quality double stranded DNA and minimize introduction of sequence error.

PCR amplifies portions of the first 9 and second 10 nucleic acid populations into double stranded DNA, and has the drawback that PCR tends to introduce errors into the amplified sequences. One preferred strategy in the use of PCR is to employ a short oligonucleotide of arbitrary sequence in combination with an oligo-dT oligonucleotide, for example under conditions described for techniques of Differential Display (see, for example, Liang et al. *Science* 257:967, 1993; U.S. Pat. No. 5,262,311, each of which is incorporated herein by reference). The primers need not be radioactively labelled, but it is preferable that one is biotinylated so that the PCR product is biotinylated at one end. Of course, if a gene or region of known sequence is being analyzed, it may be desirable to employ PCR and amplify substantially only that gene through the use of specific primers, one of which is preferably biotinylated.

As depicted in FIG. 1, first and second nucleic acid populations 9, 10 are mixed together, preferably in roughly equal proportions, to produce a nucleic acid mixture 12 that is subsequently exposed to denaturing conditions (e.g., to temperatures above about 90° C., or to a denaturing agent such as sodium hydroxide) so that individual nucleic acid strands within the mixture are separated from one another (see, for example, Cotton et al. *Proc. Natl. Acad. Sci. USA* 85:4397, 1988; Shenk et al. *Proc. Natl. Acad. Sci. USA* 72:989, 1975; Steger *Nuc. Acids Res.* 22:2760, 1994 each of which is incorporated herein by reference). The mixture is then exposed to annealing conditions so that individual strands anneal to one another, and heteroduplexes, containing one strand from the first nucleic acid population and one strand from the second nucleic acid population, are formed (see Cotton et al., supra; Shenk et al., supra). According to the present invention, at least one heteroduplex contains a mismatch 11.

One of ordinary skill in the art will recognize that, if the duplexes in the first nucleic acid population 9 are labelled AA' and the duplexes in the second nucleic acid population 10 are labelled aa', the nucleic acid mixture 12, after the denaturing and annealing steps, contains duplexes AA' and aa', as well as heteroduplexes Aa' and aA'. The AA' and aa' duplexes contain no mismatches and are indistinguishable from the AA' and aa' duplexes present in the first and second nucleic acid populations 9, 10. The Aa' and aA' heteroduplexes contain one or more mismatches or hairpin loops if they include nucleotide sequences that differ between the first 9 and second 10 nucleic acid populations. Only mismatch-containing duplexes are cleaved in subsequent steps.

One of ordinary skill in the art will also recognize that, in the embodiment depicted in FIG. 1, the motivation for mixing first 9 and second 10 nucleic populations in roughly equal proportions, rather than in some other ratio, is a desire to maximize production of heteroduplexes. With a 1:1 ratio, approximately 50% of the double stranded molecules in the nucleic acid mixture 12 will be heteroduplexes after denaturation and reannealing. Other ratios can be used, of course, as long as heteroduplexes are formed, but roughly equal proportions are preferred.

One of ordinary skill in the art will also recognize that the relative order of the mixing and denaturation steps is not critical, so long as denatured molecules are contacted with one another under conditions appropriate for reannealing and heteroduplex formation.

In some cases, the duplexes formed after denaturation and annealing may be incomplete. That is, one strand in the duplex may be longer than the other so that the duplex has a single-stranded "tail" or "overhang". For example, mRNA degradation, premature termination of reverse transcription, and/or amplification errors can result in production of a truncated strand (or duplex) in the first 9 or second 10 nucleic acid population. When the truncated strand is mixed with and hybridized to a full-length strand, the resulting duplex will have a single-stranded tail. It is generally desirable to remove such tails before performing the cleavage reaction, in order to ensure that the tails are not cleaved (because cleavage of such a tail would produce a cleavage product that is not indicative of a sequence difference between the first 9 and second 10 nucleic acid populations).

A variety of techniques are available in the art for removal of single-stranded tails from a nucleic acid duplex. For example, in some cases, tails can be degraded by using a single-strand-specific DNase or RNase (e.g., mung bean nuclease; see Kroeker et al. *Biochemistry* 15:4463, 1976, incorporated herein by reference). Alternatively, the shorter strand can be extended, for example using a DNA polymerase (see, for example, Gubler *Methods Enzymol.* 152:330, 1987; Sambrook et al. supra pg. 5.45, each of which is incorporated herein by reference). In preferred embodiments of the invention, the duplexes in the nucleic acid mixture 12 are DNA-DNA duplexes (see above), and single-stranded overhangs are filled in with a DNA polymerase.

The next steps in the method of the present invention involve i) mismatch-dependent cleavage of mismatched heteroduplexes; and ii) separation of the cleavage products. FIG. 1 presents an embodiment of the invention in which heteroduplexes are immobilized on a solid support 14, preferably through interaction of the biotin label 6 with streptavidin 15 coated on the surface of the solid support. A variety of streptavidin-coated solid materials (e.g., glass beads, magnetic beads, chromatography matrices, plastic plates, etc.) are readily available from commercial sources that also provide descriptions of optimal buffer and reaction conditions for biotin-streptavidin coupling reactions (see, for example, Sigma, St. Louis, Mo., see 1995 catalog #52415).

After the coupling-reaction is performed, the population of immobilized heteroduplexes 13 is washed extensively and is exposed to cleavage conditions. A large number of mismatch-dependent cleavage reagents are available, some of which cleave DNA-DNA duplexes (e.g., hydroxylamine plus piperidine; osmium tetroxide plus piperidine; S1 nuclease; see Shenk et al. *Proc. Natl. Acad. Sci. USA* 79:989, 1975; Cotton et al. *Proc. Natl. Acad. Sci. USA* 72:989, 1975, each of which is incorporated herein by reference), some of which cleave DNA-RNA duplexes (e.g., RNase A; see Myers et al. *Science* 230:1242, 1985; Maniatis et al. U.S. Pat. No. 4,946,773, each of which is incorporated herein by reference), and some of which cleave RNA-RNA duplexes (see Myers et al., supra; Maniatis et al., supra).

Reaction conditions vary for different reagents, and optimal conditions are generally described in materials provided by the commercial suppliers of individual reagents (see, for example, Ambion, Austin Tex., 1994/95 catalog #1415). Reliable procedures for chemical or enzymatic cleavage of mismatch-containing DNA-DNA or DNA-RNA hybrids are also described in the literature (see, for example, Cotton et al., *Proc. Natl. Acad. Sci. USA,* 85:4397, 1988; Shenk et al., *Proc. Nat. Acad. Sci. USA* 72:989, 1975; Myers et al. supra; Maniatis et al. U.S. Pat. No. 4,946,773, each of which is hereby incorporated by reference). As discussed above, in preferred embodiments of the invention, the duplexes are double-stranded DNA at this point, so that use of DNA cleavage agents is appropriate.

Following the cleavage step, the cleaved nucleic acids 16 are preferably treated with fresh streptavidin-coated solid support. Although this step is not essential, it is desirably performed in order to re-bind any biotinylated nucleic acids that may have dissociated from the original solid support during the cleavage reaction.

Cleavage products are separated from one another by any of a variety of available techniques. As depicted in FIG. 1, cleavage frees certain fragments 17 from the solid support, so that they pass into solution. Each freed fragment 17 has one end that is produced by the cleavage reaction, which occurs at or near the mismatch. The freed fragments 17, present in the solution phase, are separated from the solid support through a separation procedure appropriate to the type of solid phase. For example, where the solid phase is glass beads, the solid phase can be separated from the solution by, for example, centrifugation; where the solid phase is magnetic beads, a magnetic field can be used to effect separation; where the solid phase is a chromatography matrix, the solid and solution phases are separated by repeated washing; etc. A worker of ordinary skill in the art will be aware of various separation strategies appropriate for different types of solid phases.

Freed fragments 17, isolated with the solution phase, are used to identify the point (or points) of mismatch that represent sequence differences between the original first 9 and second 10 nucleic acid populations. As mentioned above, one end of each freed fragment corresponds to the location of a sequence alteration between the two nucleic acid populations. Freed fragments 17 can therefore be used as probes or primers to screen gene libraries and identify genes in which sequence differences occur. Alternatively or additionally, sequence information from freed fragments 17 can be used to identify the relevant genes, through analysis of genetic databases. In some cases, it may be possible to directly sequence an isolated fragment 17, to directly label an isolated fragment 17 for use as a probe, or to use an individual isolated fragment 17 itself as a primer. More likely, however, it will first be necessary to amplify the particular fragment, for example, by cloning.

A wide variety of cloning vectors are available that replicate in a host cell, and techniques for introducing foreign DNA fragments into a cloning vector are well established, even when the nucleotide sequence of the fragment to be cloned is unknown, as is the case here (see, for example, Klickstein et al. *Current Protocols in Molecular Biology*, Ausubel et al. eds, John Wiley & Sons, New York, N.Y., 1995, pp 5.5.1–5.5.14, incorporated herein by reference).

Vectors are available that are specifically designed to allow easy sequence determination (e.g., Promega, Madison, Wis., 1994/95 catalog #P2211, #P2551), easy production of RNA probes (e.g., Promega, Madison, Wis. 1994/95 catalog #P2129, #P2221, #P1091, #P1101, #P1241, #P2211, #P2551, #Q6301, #Q6121, #Q6111; see also RNA probe production kits from Promega, Madison, Wis. 1994/95 catalog #P1280, #P1300, #P1290, #P2020, #P1270, #P1071, #P1250, #P2580, #P2590), easy expression of polypeptides encoded by cloned products (e.g., Promega, Madison, Wis. 1994/95 catalog #P2211, #P2551, #Q6111; see also in vitro translation kits from Promega, Madison, Wis. 1994/95 catalog #L4540, #L4970, #L4152, #L4330, #L4140, #L4410, #L1030, #L1020), etc. DNA probes can be made using any of these vectors, for example, by cutting out the cloned insert and labelling it using nick translation or random priming methods (see, for example, Sambrook et al., supra, Chapter 10, incorporated herein by reference).

Cloned material is introduced into an appropriate host cell, and replicated therein, according to known procedures (see, for example, Sambrook et al. supra, pp. 1.74–1.75, incorporated herein by reference). Specific vectors are available that are designed to replicate in virtually any host cell, such as a bacterial cell, a yeast cell, a mammalian cell, a fruit fly cell, etc. (see, for example, Invitrogen, San Diego, Calif. 1995 catalog #V780-20, #V044-50, #V004-50; see also Yates et al. *Nature* 313:812, 1985, incorporated herein by reference).

Cloning inherently separates individual isolated fragments from one another. In some cases, however, it may be desirable to perform at least one separation step prior to cloning. For example, the population of isolated fragments 17 can be analyzed by gel electrophoresis, and fragments of a particular size, or range of sizes, can be separated from fragments of different sizes. Individual size-fractionated populations can then be cloned into vectors.

In preferred embodiments of the present invention, isolated fragments 17 are cloned into an appropriate vector, replicated in a host cell, and re-isolated for sequencing and/or screening studies. DNA sequencing is a routine procedure, and many protocols and reagents are readily available in the art (see, for example, Sequenase Kit from United States Biochemical, Cleveland, Ohio, 1994/95 Catalog #70770, #71350, and #70700). Also, screening procedures are available for analyzing clones obtained according to the present invention without direct sequencing (see, for example, Myers et al., *Nature* 313:495, 1985; Cotton et al., *Proc. Natl. Acad. Sci. USA* 85:4397, 1988; Myers et al., *Science* 230:1242, 1985; Orita et al., *Proc. Natl. Acad. Sci. USA* 86:2766, 1989, each of which is incorporated by reference). Clones obtained according to the present invention can also be used to screen, for example, cDNA or genomic libraries according to known techniques.

Techniques for screening libraries using at least one primer designed based on the sequence of the isolated fragment are also known, as are techniques for producing genomic or cDNA libraries from cells (see Sambrook et al. supra, Chapters 8 and 9, incorporated herein by reference). As is known in the art, effective library screening requires stringent hybridization conditions. Many suitable sets of stringent hybridization conditions are available in the literature (see, for example, Sambrook et al. supra Chapter 8).

Once the gene to which the isolated fragment corresponds is identified, it is generally worthwhile to clone the gene (or a portion thereof) from the first 1 and second 2 cells in order to confirm that a sequence difference is in fact present at the appropriate location and was not a result of the experimental manipulations performed during the practice of the invention.

Also, it is generally valuable to search available genetic sequence databases (such as, for example, GenBank, EMBL, DDBJ) in order to determine whether or not the identified gene was previously known. The present invention allows identification of at least partial sequence of a gene whose nucleotide sequence differs in the first 1 and second 2 cells. Techniques are readily available in the art that allow cloning of a complete gene once partial sequence has been identified (see, for example, Sambrook et al. supra, Chapters 8 and 9; Klickstein et al. *Current Protocols in Molecular Biology*, Ausubel et al, eds, John Wiley & Sons, New York, N.Y., 1995, Chapter 5, each of which is incorporated herein by reference).

One of ordinary skill in the art will appreciate that the foregoing description of techniques for identifying sequence differences in mRNA populations according to the present invention represents a description of certain preferred embodiments of the invention. Various changes and modifications can be made without departing from the spirit or scope of the present invention.

For example, it will be understood by a worker of ordinary skill in the art that the methods of the invention can be used to compare any number of nucleic acid populations (greater than two). The embodiment depicted in FIG. 1 shows isolation of mRNA samples from two cells, but more than two cells could equally well be analyzed.

Also, the above discussion makes clear that the present invention is not limited to analyses of DNA-DNA duplexes. That is, the first 3 and second 4 MRNA populations need not be converted into DNA-DNA duplexes in order to be compared. Any nucleic acid duplex for which a cleavage reagent is available can be studied according to the present invention. Mismatch-containing DNA-RNA duplexes can be produced, for example, by reverse transcribing only one of the first 3 and second 4 mRNA populations into cDNA and hybridizing the resulting cDNA strands directly with the non-reverse-transcribed second 4 or first 3 mRNA population. Mismatches in DNA-RNA hybrids are identified by cleavage with RNase A, which breaks the RNA strand but not the DNA strand (see further discussion below).

Where the freed fragments 17 are DNA-RNA hybrids, it is generally desirable to convert them to DNA-DNA duplexes for further processing. Various techniques are available to accomplish this. For example, the DNA-RNA duplex can be denatured and subsequently treated with either DNase or RNase, as desired, to remove either the DNA or the RNA strand (see, for example, Sambrook et al., supra pp. 1.51–1.52; Gilman *Current Protocols in Molecular Biology*, Ausubel et al., eds, John Wiley & Sons, N.Y., pp. 4.1.4–4.1.6, 1995, each of which is incorporated herein by reference). A poly-A tail can then be added to the remaining strand, using terminal deoxynucleotide transferase if the remaining strand is DNA (see, for example, Flickinger et al., *Nuc. Acids Res.* 20:2382, 1992, incorporated herein by reference), or poly-A polymerase if the remaining strand is RNA (see, for example, Tabor, *Current Protocols in Molecular Biology*, Ausubel et al., eds., John Wiley & Sons, N.Y. pp. 3.9.1–3.9.2, 1987, incorporated herein by reference). The single-stranded DNA or RNA is then converted to double-stranded DNA according to known procedures that utilize the poly-A tail (see, for example, Klickenstein et al. *Current Protocols in Molecular Biology*, Ausubel et al., eds, John Wiley & Sons, N.Y., pp. 5.5.1–5.5.14, 1995, incorporated herein by reference).

RNA-RNA hybrids can also be produced and analyzed according to the present invention, if that is desired (for discussion of RNA-RNA duplex cleavage, please see Myers et al. *Science* 230:1242, 1985; Maniatis et al. U.S. Pat. No. 4,946,773, each of which is incorporated herein by reference). Mismatch-containing RNA-RNA duplexes can be produced by reverse transcribing either the first 3 or second 4 mRNA population into cDNA, converting the resulting mRNA-cDNA duplexes into DNA-DNA duplexes, cloning the DNA-DNA duplexes into an appropriate vector that allows production of mRNAs anti-sense to the original first 3 or second 4 mRNA population, transcribing the insert-containing vectors, and hybridizing the transcribed anti-sense mRNA strands with the non-anti-sense second 4 or first 3 mRNA population (see, for example, Sambrook et al., pp. 5.58–5.59, incorporated herein by reference). Appropriate transcription vectors include any vectors containing a promoter such as, for example, a SP6, T7, or T3 RNA polymerase promoter (see, for example, Promega, Madison Wis., 1994/95 catalog #P2129, #P2221, #P1091, #P1101, #P1241, #P2211, #P2551, #Q6301, #Q6121, #Q6111). Kits for producing RNA from such vectors are commercially available (see, for example, Promega, Madison, Wis., 1994/95 catalog #P1280, #P1300, #P1290, #P2020, #P1270, #P1071, #P1250, #P2580, #P2590).

One of ordinary skill in the art will also recognize that certain modifications can be made in individual steps of the above-described preferred embodiment of the present invention. For example, in the embodiment depicted in FIG. 1 and discussed above, a biotinylated poly-T primer is utilized as a primer for reverse transcription during synthesis of the first cDNA strand complementary to the mRNA. A biotinylated poly-T primer was selected in order to allow nucleic acid duplexes including the primer to be readily attached to a solid phase. Alternative solid-phase coupling means could be used instead or could be left off entirely (see below). Also, the primer could be coupled to the solid phase prior to the reverse transcription step if desired, particularly if the solid phase is comprised of small particulates such as glass beads.

The use of a poly-T primer in the reverse transcription step described above allows synthesis of a first cDNA strand corresponding each and every polyadenylated mRNA transcript isolated from cells 1 and 2. Such a primer is useful when it is desirable to compare the nucleotide sequence of substantially every expressed gene (whose transcript gets polyadenylated) in two or more cells. Short primers of random sequence have also been used successfully to prime synthesis of a cDNA strand corresponding to each mRNA in a population. Preferably, these short primers are within the range of approximately 6–12 nt in length, though any short primer capable of priming cDNA synthesis is useful.

Of course, it may not always be necessary or desirable to copy each and every transcript, so that a more specific primer, for example corresponding to a consensus nucleotide sequence found in a gene family, could be used for reverse transcription. Many such consensus sequences are known and studies have reported successful use of primers corresponding to gene family consensus sequence (see, for example, Neri et al. *Cell* 67:1075, 1991; Schmid et al. *Nature* 352:733, 1991; Shen et al. *Nature* 352:736, 1991; Levy-Lahad et al. *Science* 269:973, 1995, each of which is incorporated herein by reference).

Also, we mentioned above that poly-T reverse transcription primers for use in the present invention are preferably between about 16–20 nucleotides in length. The exact length of the reverse transcription primer is not essential to the present invention so long as the primer selected specifically primes reverse transcription under the reaction conditions employed. Poly-T primers of various lengths that are suitable for use in the reverse transcription step are available from commercial sources (see, for example, New England Biolabs, Beverly, Mass., 1995 catalog page 111).

The above discussion also describes an isolation process that involves securing duplexes to a solid phase so that soluble cleavage products can readily be separated therefrom. The embodiment depicted in FIG. 1 and discussed above utilizes a biotin-streptavadin interaction to immobilize duplexes on a solid phase. Other immobilization techniques are well known in the art and can readily be utilized in the practice of the present invention. For example, nucleic acids can be immobilized on poly(ethyleneimine)-modified nylon beads using cyanuric acid as the coupling reagent (see, for example, Ness et al. *Nuc. Acids Res.* 19:3344, 1991, incorporated herein by reference). Alternatively, carbodiimide-mediated end-attachment either of 5'-phosphate to amino magnetic beads or of 5'-$NH_2$-modified nucleic acids to carboxyl magnetic beads can be utilized (see, for example, Lund et al., *Nuc. Acids Res.* 16:10861, 1988, incorporated herein by reference).

It is not critical that the duplexes be attached to the solid phase through an interaction at one end of the duplex. Multiple closely-located attachment points are also acceptable. Or, the duplexes can be attached at both ends (see below). Any attachment point or means that does not interfere with the separation of cleavage products is effective.

Moreover, there is no absolute requirement in the present invention that duplexes be attached to a solid phase. So long as cleavage products can be identified and/or isolated, they can be used to identify the genes to which they correspond. For example, cleavage products can be isolated from biotin-labelled molecules by immunoprecipitation or phenol-chloroform extraction. Immunoprecipitation can be accomplished, for example, by using a streptavidin-conjugated primary antibody to precipitate all biotin-labelled molecules (see, for example, Springer, *Current Protocols in Immunology*, Coligan et al., eds, John Wiley & Sons, N.Y., pp. 8.3.1.–8.3.11, 1991, incorporated herein by reference). Cleavage products are not precipitated.

Similarly, phenol-chloroform extraction can be used to solubilize biotinylated molecules that are interacting with streptavidin. In fact, nucleic acid molecules conjugated to or interacting with any protein can be extracted from non-protein-associated molecules such as cleavage products, by extraction with 1:1 phenol-chloroform (see Invitrogen, San Diego, Calif. 1995 catalog page 63).

Of course, where the cleavage reaction breaks only one of the two strands of the heteroduplex, as is the case with some chemical cleavage agents (see Cotton et al. *Proc. Natl. Acad. Sci. USA* 85:4397, 1988, incorporated herein by reference) and with RNase A when used to treat RNA-DNA duplexes (see Myers et al. *Science* 230:1242, 1985; Maniatis et al. U.S. Pat. No. 4,946,773, each of which is incorporated herein by reference), fragments 17 are separated from the immobilized heteroduplexes 13 under denaturing conditions such as temperatures above 90° C. or exposure to a denaturant such as 0.15N NaOH (see Hultman et al. *Nuc. Acids Res.* 17:4937, 1989, incorporated herein by reference). One of ordinary skill in the art will recognize that exposure to NaOH is not appropriate when the fragments 17 are RNA, as RNA degrades in NaOH.

Various additional modifications to the procedures described above in the discussion of the embodiment depicted in FIG. 1 are required when the cleavage reaction breaks only one of the two strands. For example, if only one strand of the heteroduplex is cleaved, both strands should have been immobilized, and fragments 17 produced by cleavage should be separated from the immobilized heteroduplexes 13 under denaturing conditions such as temperatures above 90° C. or exposure to a denaturant such as 0.15N NaOH (see Hultman et al. *Nuc. Acids Res.* 17:4937, 1989, incorporated herein by reference). Of course, exposure to NaOH is not appropriate when the fragments 17 are RNA, as RNA degrades in NaOH.

In a preferred single-strand cleavage embodiment of the present invention, both heteroduplex strands are labelled with biotin and are subsequently immobilized on a streptavidin-coated solid phase as discussed above. At least two methods are available that allow biotinylation of both strands of a DNA-DNA heteroduplex. In the first method, a biotinylated poly-T primer such as that depicted in FIG. 1 is utilized whose sequence includes a rare restriction site at its 5' end. The primer is preferably biotinylated either in the restriction recognition sequence or at the poly-T portion. Of course, the primer should be biotinylated in such a way that biotinylation does not interfere with restriction digestion, and that at least one biotinylated nucleotide is retained on the primer after cleavage (i.e. at least one labelled nucleotide is located 3' of the cleavage site).

Rare restriction sites are discussed in Lindsay et al. *Nature* 327:336, 1987 and Sambrook et al. supra pp. 5.27, 1989, each of which is incorporated herein by reference. The NotI site (GCGGCCGC) [SEQ ID NO: 1] is preferred because it occurs only once in every 1,000,000–1,500,000 basepairs in the mammalian genome, and is therefore unlikely to be present in the middle of a cDNA of interest. Also, cleavage by NotI produces a 5' overhang, so the cut site can be filled in with a DNA polymerase. The primer preferably includes a segment of arbitrary sequence that is several nucleotides long and is located 5' of the restriction site, because such a sequence may facilitate digestion (see New England Biolabs, Beverly, Me. 1995 catalog, pp. 208–209).

The above-mentioned primer is used to make a cDNA copy of the isolated mRNA as described above. The cDNA-mRNA duplex is then converted into double-stranded DNA as described above. Subsequently, the double-stranded DNA is digested with NotI (or other relevant restriction enzyme), and the cut site is filled in with biotinylated nucleotides according to known procedures (see Gibco BRL, Grand Island, N.Y., 1995 catalog #19509-017, #19524-016, and #19518-018). Of course, the particular biotinylated nucleotides employed should be those required to fill in the overhang left after cleavage. To fill in a NotI cleavage site, dATP, dGTP, dTTP, and biotin-14-dCTP or biotin-14-dGTP are used.

In the second method for producing DNA duplexes with two biotinylated strands, a biotinylated poly-T primer is utilized whose sequence includes a restriction site at which cleavage is blocked by chemical modification such as methylation. In preferred embodiments of this method, the primer includes an XhoI site (CTCGAG) [SEQ ID NO: 2]. XhoI does not cleave its site if the cytosine residues are methylated (Sambrook et al. supra, pp. 5.23–5.26, incorporated herein by reference). This primer is utilized to make the first cDNA strand from the mRNA template, as described above, except that 5-methyl-dCTP is utilized in the reverse transcription reaction instead of dCTP. After synthesis of the first cDNA strand, unincorporated methylated nucleotides are preferably removed, e.g. by spin column, and the second cDNA strand is synthesized with normal dCTP. The double-stranded cDNA is then digested with XhoI so that the site in the primer is cleaved, but no other site is cleaved. The 5' overhang produced by cleavage with XhoI is then filled in using biotinylated nucleotides, as described above (see also Klickstein et al. *Current Protocols in Molecular Biology*, Ausubel et al., eds, John Wiley & Sons, N.Y., 1995, pp. 5.5.6–5.5.8, incorporated herein by reference).

The first method for producing DNA duplexes labelled on both strands is preferred over the second because the second requires a special nucleotide, which may be expensive. Moreover, the cDNA strand including the modified nucleotide may have altered, undesirable, physical and/or chemical properties.

DNA-RNA heteroduplexes for use in the present invention can also be labelled on both strands. For example, if the first mRNA population 3 is reverse transcribed into cDNA using a biotinylated primer as described above in the discussion of FIG. 1, and the second mRNA population 4 is not reverse transcribed but rather is biotinylated through addition of, for example, biotin-14-ATP to the end of the poly-A tails using poly-A polymerase (see, for example, Tabor, *Current Protocols in Molecular Biology*, Ausubel et al., eds, John Wiley & Sons, N.Y., 1987, pp 3.9.1–3.9.2, incorporated herein by reference), then the cDNAs produced from reverse transcription of the first mRNA population 3 can be hybridized with the biotinylated mRNAs in the second mRNA population 4 to produce mismatch-containing DNA-RNA heteroduplexes that are labelled on both strands.

Prior to hybridization of the labelled cDNA strands with the labelled second mRNA population 4, it may be desirable to remove the first population mRNAs, for example, by digestion with RNase, but care must be taken to remove all RNase from the remaining, labelled cDNA strands before the labelled cDNA strands are incubated with the second mRNA population 4.

RNA-RNA heteroduplexes labelled on both strands can also be produced according to available techniques. For example, each of the RNA strands to be hybridized can be biotinylated at its 3' end through addition of biotin-14-ATP by poly-A polymerase. Hybridization of sense RNA strands (e.g. in the first mRNA population 3) with antisense RNA strands (e.g. produced from the second mRNA population 4) produces doubly-labelled heteroduplexes. Both ends of such a doubly-labelled RNA-RNA heteroduplex will become attached to the streptavidin-coated immobilization surface, but fragments can nonetheless be isolated (as single-stranded RNA) through denaturation of the immobilized RNA-RNA heteroduplex.

The worker of ordinary skill in the art will be aware of other modifications that may be made to the above-described techniques during the practice of the present invention. In particular, various modifications may be made, or control reactions run, in order to reduce the effects of background cleavage events on the reactions of the present invention. One of ordinary skill in the art will be aware of such changes, and such modified procedures are within the scope of the present invention.

EXAMPLE 1

Detection of Sequence Difrerences in mRNA Populations

Isolation of mRNA

The isolation of mRNA is essentially as described (Xie et al., BioTechniques 11:324, 1991). In brief, $40 \times 10^6$ of murine NIH 3T3 cells are washed 3 times with cold phosphate-buffered saline (PBS) and lysed in 1.6 ml solution of 1.9M guanidinium thiocyanate/12 mM sodium citrate/50 mM NaOAc/50% phenol/0.36% 2-mercaptoethanol(pH 7.0). 0.16 ml of chloroform/isoamyl alcohol (24:1) is added to the lysate and mixed. The mixture is kept on ice for 30 minutes and centrifuged at 12,000×g for 20 minutes at 4° C. to separate the phases. The upper aqueous phase is transferred to a fresh 2 ml tube containing 0.8 ml isopropanol. The mixture is then placed at −20° C. for 1 hour and centrifuged at 12,000×g for 15 minutes at 4° C. Pelleted RNA is washed twice with 70% ethanol and air dried. The total RNA is then resuspended in 100 μl of DEPC-treated water. Poly(A) mRNA is isolated using Stratagene Poly(A) Quick mRNA Isolation Kit (Stratagene, La Jolla, Calif.). The $OD_{260/280}$ of the poly(A) mRNA is measured to determine its concentration.

Producing two populations of mRNA containing a single base difference

To establish the optimal conditions for detecting sequence differences in two populations of mRNA, a system is established as described below. Two separate in vitro mutagenesis procedures are carried out on chloramphenicol acetyltransferase (CAT) gene carried on plasmid pCAT (Promega, Madison, Wis.) using Chameleon mutagenesis kit (Stratagene, La Jolla, Calif.). A single EcoRI site GAATTC [SEQ ID NO: 3] in the CAT gene is changed to GAAATC (sequence A) [SEQ ID NO: 4] and GAAGTC (sequence B) [SEQ ID NO: 5]. The two altered CAT sequences are subcloned into pSP64 Poly(A) plasmid vector at the polylinker SalI site (Promega) under transcriptional control of the SP6 promoter. Two CAT poly(A) RNAs are produced using RiboMax RNA production systems (Promega). 0.4 ng of each CAT poly(A) RNA is mixed with 4 μg of the 3T3 mRNA separately to yield two populations of mRNA which have at least one base difference at an appropriate proportion.

First strand cDNA synthesis

The two populations of mRNA with the sequence A and sequence B are parallel processed from now on till indicated in later step. 4 μg of the Poly(A) mRNA is suspended in 10 μl water and heated to 68° C. for 2 minutes. The mRNA is then added to a reaction buffer containing primer 5'-ATAAGAATGCGGCCGCTTTTTTTTTTTTTTTTTTT-3' [SEQ ID NO: 6] at the concentration of 5 μM. The primer contains NotI sequence GCGGCCGC [SEQ ID NO: 1] and 2 or 3 arbitrary distributed biotinylated thymidine residues in the poly-dT region. The reaction buffer contains 50 mM Tris-HCl pH 7.6, 70 mM KCl, 10 mM MgCkl₂, 1 mM each of dNTPs, 0.4 mM dithiothreitol, 25 units RNase inhibitor and water to final volume of 100μl. 400 units of M-MLV reverse transcriptase is added to the reaction mixture and the reverse transcription reaction is carried out at 37° C. for 1 hour.(Sambrook et al., *Molecular Cloning: A Laboratory Manual*, Second Edition, Cold Spring Harbor Press, Cold Spring Harbor, N.Y., pp.8.60, 1989)

Second strand cDNA synthesis

Add followings directly to the first-strand reaction: 140 μl of 10 mM $MgCl_2$, 10 μl of 2M Tris-HCl(pH 7.4), 3 μl of 1M $(NH_4)_2SO_4$, 2 units of RNase H and 90 units of *E. coli* DNA polymerase. The reaction mixture is incubated at 16° C. for 4 hours followed by addition of 2.0 μl of 50 mM NAD and 200 units of *E.coli* DNA ligase. The reaction mix is then incubated at 23° C. for 15 minutes. The synthesized double stranded cDNA is ethanol precipitated and dried. (Sambrook et al., *Molecular Cloning. A Laboratory Manual*, Second Edition, Cold Spring Harbor Press, Cold Spring Harbor, N.Y., pp.8.64, 1989)

Digestion with NotI

The cDNA is resuspended in 100 μl of NotI buffer containing 100 mM NaCl, 50 mM Tris-HCl(pH 7.9), 10 mM $MgCl_2$, 1 mM dithiothreitol and 100 μg/ml BSA. 20 units of NotI is added and the digestion is carried out at 37° C. for 2 hours (the enzyme and buffer are purchased from New England Biolabs).

Filling the NotI overhang with biotinylated nucleotide 3 units of DNA polymerase I Klenow fragment is added to the NotI digestion mixture. Nucleotides dATP, dGTP, dTTP, as well as Biotin-14-dCTP are added to final concentration of 50 μM each. The reaction mixture is incubated at 37° C. for 15 minutes. The DNA is precipitated with ethanol.

Removal of alternatively spliced transcripts

The DNA is suspended in 100 μl of mung bean nuclease buffer containing 50 mM sodium acetate(pH 5.0), 30 mM NaCl and 1 mM $ZnSO_4$. The mixture is heated at 90° C. for 5 minutes on a PCR machine. The temperature is reduced to 80° C., then slowly decreased to 42° C. at the rate of 0.5° C./minute, and kept at 42° C. for 2 hours. 4 units of mung bean nuclease is added and the digestion reaction is carried out at 30° C. for 30 minutes. The mixture is extracted with 100 μl of phenol-chloroform twice. The above denaturing, annealing and mung bean nuclease digestion procedure is repeated once or, if necessary, twice. The DNA is ethanol precipitated and dried.

Formation of heteroduplex from two populations of cDNA

The two populations of double stranded cDNA with the sequence A and sequence B are mixed 1:1 to a final volume of 100 μl in 0.3M NaCl/3.5 mM $MgCl_2$/3 mM Tris-HCl(pH 7.7) and heated at 95° C. for 5 minutes on a PCR machine. The temperature is then reduced to 80° C. and slowly decreased at the rate of 0.5° C./minute to final temperature of 42° C. and kept at 42° C. for 2 hours. The DNA is precipitated with ethanol.

Elimination of single-stranded tail

The annealed cDNA is suspended in 100 μl of T4 DNA polymerase buffer containing 50 mM Tris-HCl(pH 8.3), 10 mM $MgCl_2$, 1 mM dithiothreitol, 50 mM NaCl, 100 μM each dNTPs. 5 units of T4 DNA polymerase is added and the reaction mixture is incubated at 23° C. for 30 minutes. The reaction is stopped by EDTA at 20 mM (Gubler, *Methods in Enzymology* 152:330, 1987).

Immobilization of the annealed DNA to solid support

75 μg of streptavidin magnetic beads (SIGMA, St. Louis, Mo.) are added to the stopped T4 DNA polymerase reaction and incubated, with shaking, at 23° C. for 20 minutes. The beads are rinsed twice in 0.5 ml 0.5× SSC (Rhoer-Moja et al., *Analytical Biochemistry* 213:12, 1993) and then once in distilled water.

Mismatch-dependent chemical cleavage of the immobilized DNA

All solutions are prepared as described in Saleeba et al., *Methods in Enzymology* 217:286, 1993. For cytosine modification, the magnetic beads with immobilized DNA are suspended in 100 μl of hydroxylamine solution (1.39 g hydroxylamine hydrochloride in 1.6 ml distilled water and 1.75 ml diethylamine, with final pH 6.0), incubated for 30 minutes at 37° C. with shaking, and stopped at 4° C. The magnetic beads are separated from the hydroxylamine solution and rinsed twice with distilled water. The magnetic beads with immobilized DNA are then suspended for thymidine modification in 100 μl of osmium tetroxide solution (0.5 g osmium tetroxide in 12.5 ml distilled water in a glass container), incubated at 37° C. for 3 minutes with shaking, and stopped at 4° C. The osmium tetroxide solution is removed from the magnetic beads. The beads are rinsed twice with distilled water. The dried magnetic beads are suspended in piperidine solution (1:10 diluted in distilled water before use), heated at 90° C. for 30 minutes with shaking. The piperidine solution is separated from the magnetic beads at 90° C. at the end of the incubation. The piperidine solution, which contains cleaved DNA, is frozen and lyophilized. The cleaved DNA is suspended in 30 μl of 50 mM NaCl/10 mM Tris-HCl(pH 8.3)/10 mM MgCl$_2$/1 mM dithiothreitol. 30 μg of fresh streptavidin magnetic beads are added and incubated with shaking at 23° C. for 20 minutes, then removed from the solution and discarded. The DNA is precipitated with ethanol.

Addition of homopolymer tail to the cleaved DNA

The cleaved DNA is suspended in 20 μl of buffer containing 100 mM potassium cacodylate, 30 mM Tris-HCl(pH 7.0), 1 mM CaCl$_2$, 0.1 mM dithiothreitol, 0.1 μM dCTP and 20 units of terminal deoxynucleotidyl transferase (Gibco BRL, Grand Island, N.Y.). The reaction is carried out at 37° C. for 2 minutes followed by phenol-chloroform extraction and ethanol precipitation (Nelson et al., *Methods in Enzymology* 68:41, 1979). The temperature and incubation time for the transferase reaction are empirically determined to ensure formation of homopolymer tail with average length of 15 to 20 nucleotides (Michelson et al., *Journal of Biological Chemistry* 257:14773, 1982).

Formation of double-stranded DNA

The cleaved DNA fragments with homopolymer tail are mostly single-stranded and need to be converted to double-stranded DNA for subsequent cloning. The DNA is suspended in 20 μl of T4 DNA polymerase buffer as described above containing 0.5 μM of poly-dG$_{12-18}$ and 1 unit of T4 DNA polymerase. The reaction mixture is incubated at 23° C. for 30 minutes. The reaction is then stopped by EDTA at 20 mM. The DNA is precipitated with ethanol.

Ligation of linker to blunt-ended DNA

The DNA is suspended in 20 μl of ligation buffer containing 66 mM Tris-HCl(pH 7.6), 5 mM MgCl$_2$, 5 mM dithiothreitol, 0.5 mM ATP. SalI linker 5'-CGGTCGACCG-3' [SEQ ID NO. 7] (New England Biolabs, Beverly, Mass.) is added to final concentration of 5 μM, and 2 Weiss units of T4 DNA ligase is added. Incubate the reaction for 16 hours at 16° C. The DNA is precipitated with ethanol and then resuspended in 20 μl of SalI digestion buffer containing 150 mM NaCl, 10 mM Tris-HCl(pH 7.9), 10 mM MgCl$_2$, 1 mM dithiothreitol, 100 μg/ml BSA and 10 units of SalI restriction enzyme. Incubate the reaction at 37° C. for 24 hours. The DNA is precipitated with ethanol.

Cloning and sequencing of the DNA

The DNA is suspended in 10 μl of ligation buffer as described above. 10 ng of SalI digested plasmid vector pGEM −3Zf(+) (Promega) and 2 Weiss units of T4 DNA ligase are added. Incubate the reaction at 16° C. for 16 hours. The ligated DNA is directly transformed into *E.coli* competent cells which are then spread on X-Gal plates. Single-stranded DNAs are made from white colonies selected from the X-Gal plates. The DNAs are sequenced using Sequenase kit and T7 sequencing primer (United States Biochemical, Cleveland, Ohio).

Identifying the mutations

The sequence of the clones are compared with that of chloramphenicol acetyltransferase gene. Considerable number of clones contain a sequence corresponding to 5' region of the CAT sequence. One end of the identified CAT partial sequence is at the altered EcoRI site.

Detecting Sequence Differences in Genomic DNA Populations

Figure 2:
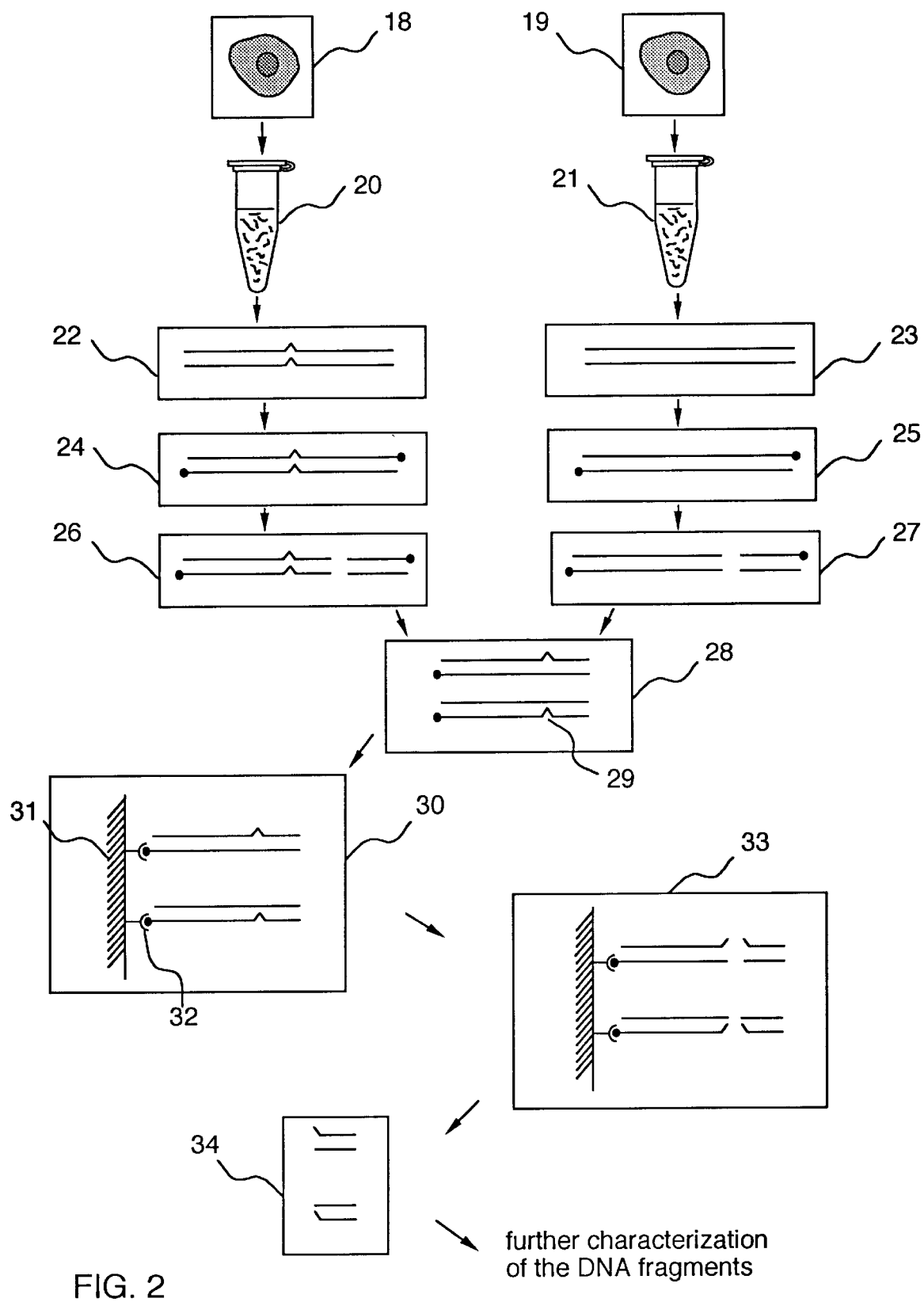
FIG. 2 is a schematic representation of a method according to the present invention for identifying sequence differences in populations of genomic DNA.

FIG. 2 presents a schematic representation of a method of detecting sequence differences in genomic DNA populations according to the present invention. Such a method is particularly useful for the analysis of sequence differences in prokaryotic cells, whose genomes are relatively small and simple, and whose RNA transcripts are not polyadenylated. Thus, for the purposes of the present discussion, we characterize the first 18 and second 19 cells depicted in FIG. 2 as prokaryotic cells, though it should be understood that the approach is equally applicable, and readily adaptable, to the study of eukaryotic cells.

As shown in FIG. 2, first 20 and second 27 populations of genomic DNA are isolated from first 18 and second 19 cells, respectively according to known techniques (see, for example, Wilson, *Current Protocols in Molecular Biology*, Ausubel et al., eds, John Wiley & Sons, N.Y., pp. 2.4.1–2.4.5, 1994; Sambrook et al supra, pp. 9.14–9.29, each of which is incorporated herein by reference). First 20 and second 21 genomic DNA populations differ from one another in that at least one DNA sequence alteration is present in first genomic DNA population 20 as compared with second genomic DNA population 21.

The overall genetic relatedness of first 18 and second cell 19 to one another will vary depending on the desires of the researcher. Generally, it is preferred that the two cells 18, 19 be as closely related as possible so as to reduce the background number of sequence differences.

It is desirable, although not essential, that the genomic DNA duplexes present in the first 20 and second 21 genomic DNA populations be cleaved into pieces approximately several thousand basepairs in length in order to facilitate subsequent processing steps. Known techniques such as cleavage with restriction enzymes (see, for example, New England Biolabs, Beverly, Mass. 1995 catalog; United States Biochemical, Cleveland, Ohio 1995 catalog; Gibco BRL, Grand Island, N.Y. 1995 catalog, each of which is incorporated herein by reference), sonication (see, for example, Sambrook et al., supra pp. 13.26–13.27, 1989; Strauss, *Current Protocols in Molecular Biology*, Ausubel et al., eds, John Wiley & Sons, N.Y., pp 6.3.4–6.3.6, 1995 incorporated herein by reference), and partial digestion with DNase I (see, for example, Sambrook et al., supra, pp. 13.28–13.29; Anderson, *Nuc. Acids Res.* 9:3015, 1981, each of which is incorporated herein by reference), can be used to effect such fragmentation. If sonication or partial digestion with DNase I is employed, DNA ends should subsequently be made blunt-ended (see, for example, Gubler, *Methods Enzymol.* 152:330, 1987).

In the embodiment depicted in FIG. 2, first 20 and second 21 genomic DNA populations are digested with a restriction endonuclease so that first 22 and second 23 populations of genomic fragments are produced. The embodiment of the invention presented in FIG. 2, like that presented in FIG. 1, includes the immobilization of nucleic acid molecules under analysis on a solid phase. Various advantages of this immobilization are discussed above and, for simplicity, are not reiterated here. Although solid immobilization is not required, it simplifies subsequent processing and analysis steps.

As depicted in FIG. 2, first 22 and second 23 genomic fragment populations are rendered capable of interaction with a solid matrix. Specifically, the fragments are biotinylated at their 3' ends (of both strands), for example by filling in the 5' overhang, created by restriction digestion, using biotinylated nucleotides (see, for example, Gubler, *Methods Enzymol.* 152:330, 1987, incorporated herein by reference; see also Gibco BRL, Grand Island, N.Y. 1995 catalog #19509-017, #19524-016, and #19518-018 for biotinylated nucleotides). Alternatively, the fragments can be labelled at both ends of both strands by, for example, ligation of a double-stranded, biotinylated oligonucleotide to each fragment end (see, for example, Sambrook et al., supra, Appendix F, incorporated herein by reference). The length of the double-stranded, biotinylated oligonucleotide is not critical, and preferably is somewhere between 6 and 20–30 basepairs. The sequence of the oligonucleotide is preferably compatible with the 5' overhangs left by restriction digestion, but otherwise can be arbitrary. Both strands of the oligonucleotide are biotinylated.

Whatever the method of biotinylation, first 24 and second 25 populations of doubly-biotinylated fragments are produced, and each fragment in the first 24 and second 25 population is labelled at both ends. Subsequent to biotinylation, the labelled genomic fragments are again cleaved (e.g., with a restriction enzyme) so that each doubly-labelled genomic fragment is converted into two singly-labelled fragments, thereby producing first 26 and second 27 populations of singly-labelled fragments. Where the fragments are biotinylated by addition of a double-stranded, biotinylated oligonucleotide to either end (see above), it is preferred that the oligonucleotide(s) contains a recognition site for this second enzyme so that the reaction will also trim concatemerized ligated DNA.

The first 26 and second 27 populations of singly-labelled fragments are then mixed with one another, denatured, and reannealed, to produce a duplex mixture 28 containing heteroduplexes formed by the annealing of a strand from the first 26 population of singly-labelled fragments with a complementary strand from the second 27 population of singly-labelled fragments. At least one of the heteroduplexes includes a mismatch 29.

The duplex mixture 28 is preferably treated with a DNA polymerase (or a DNase) to flush the ends of any "tailed" duplexes, and is immobilized on a streptavidin (32)-coated solid surface. The immobilized DNA 30 is washed several times and is exposed to a mismatch-dependent DNA duplex cleavage agent (e.g. hydroxylamine treatment followed by piperidine treatment; osmium tetroxide treatment followed by piperidine treatment; see, for example, Cotton et al., Proc. Natl. Acad. Sci. USA 85:4397, 1988, incorporated herein by reference) as discussed above. If the biotin label was incorporated by filling-in overhanging ends (see above), cleavage agents that cut both strands of the duplex should be used; if the biotin label was incorporated by addition of a double-stranded, labelled oligonucleotide, either double-strand cleavage agents (i.e., agents that cut both strands) or single-strand cleavage agents (i.e. agents that cut only one strand) can be used. Freed fragments 34 are isolated and used to identify the genomic sequences that differ between the first 20 and second 21 genomic DNA populations. Where a single-strand cleavage agent was used, the freed fragments 34 must be isolated under denaturing conditions.

As will be apparent to one of ordinary skill in the art, various modifications can be made to the above-described procedures without departing from the spirit or scope of the present invention (see previous section). For example, it is noted above that cleavage agents that cut both strands of the duplex should be used if the biotin label was incorporated by filling-in overhanging ends. However, if it is desirable to analyze such molecules with single-strand cleavage agents, the first 24 and second 25 biotinylated fragment populations need not be digested with a restriction enzyme prior to heteroduplex formation. Instead, the two populations 24, 25 are mixed with one another, and subjected to denaturation and reannealing to produce heteroduplexes that are labelled at the 3' end of each strand. Immobilization of these doubly-labelled duplexes on the solid phase results in attachment at both ends, so that cleavage products are only isolatable under denaturing conditions (see Hultman et al., Nuc. Acids Res. 17:4937; Cotton et al., Proc. Natl. Acad. Sci. USA 85:4397, each of which is incorporated herein by reference). One potential difficulty with this embodiment of the present invention is that doubly-labelled heteroduplexes that are attached to the solid phase at both ends might be accidentally broken due to agitation of the reaction.

EXAMPLE 2

Detection of Sequence Differences in Genomic DNA Populations

Preparation of genomic DNA

Bacterial genomic DNA is prepared from $1 \times 10^9$ E. coli JM109 cells as described (Wilson et al., Current Protocols in Molecular Biology (Ausubel et al., eds) p.2.4.1, John Wiley & Sons, New York, 1994). 8 µg of the genomic DNA is digested in 200 µl of EcoRI buffer containing 50 mM NaCl, 100 mM Tris-HCl(pH7.5), 10 mM $MgCl_2$, 0.025% Triton X-100 and 40 units of EcoRI. Incubate the reaction mixture at 37° C. for 8 hours. The DNA is precipitated with ethanol.

Production of two populations of DNA containing a single base difference

4 µg of each of pSP64 Poly(A) plasmid constructs carrying the altered chloramphenicol acetyltransferase (CAT) gene sequences (sequence A and sequence B) which are constructed in the example 1 are digested in 100 µl of SalI buffer containing 150 mM NaCl, 10 mM Tris-HCl(pH 7.9), 10 mM $MgCl_2$, 1 mM dithiothreitol, 100 µg/ml BSA and 20 units of SalI restriction enzyme. Incubate the reaction at 37° C. for 8 hours. The DNA fragments containing CAT sequences are isolated on a agarose gel. The two isolated DNAs are blunt-ended using DNA polymerase I Klenow fragment and dNTPs as described in the example 1. EcoRI linker 5'-CGGAATTCCG-3' [SEQ ID NO.8] (New England Biolabs) is added at final concentration of 5 µM with each CAT DNA fragments to 50 µl of ligation buffer containing 66 mM Tris-HCl(pH 7.6), 5 mM $MgCl_2$, 5 mM dithiothreitol, 0.5 mM ATP and 2 Weiss units of T4 DNA ligase. The ligation is carried out at 16° C. for 16 hours. The ligated DNA is digested with 20 units EcoRI at 37° C. for 5 hours in 100 µl buffer containing 50 mM NaCl, 100 mM Tris-HCl(pH7.5), 10 mM MgCl, and 0.025% Triton X-100. The DNA is precipitated with ethanol. 0.4 ng of each CAT DNA fragments is mixed with 4 µg of the EcoRI digested bacterial genomic DNA separately to yield two populations of DNA which have at least one base difference at an appropriate proportion.

Ligation of biotinylated linker

A pair of complementary biotinylated PvuII-EcoRI adapters 5'CCAGCTGCG-3' [SEQ ID NO: 9] and 5'-AATTCGCAGCTGG-3' [SEQ ID NO:10] the lower case indicates the biotinylated nucleotide) are ligated to each population of DNA using T4 DNA ligase as described above. The DNAs are then digested with 40 units of restriction enzyme PvuII in 100 µl of digestion buffer containing 50 mM NaCl, 10 mM Tris-HCl(pH 7.9), 10 mM $MgCl_2$ and 1 mM dithiothreitol at 37° C. for 5 hours. The DNAs are precipitated with ethanol.

Formation of heteroduplex from two populations of DNA

The two populations of DNA with the sequence A and sequence B are mixed 1:1 to a final volume of 100 µl in 0.3M NaCl/3.5 mM $MgCl_2$/3 mM Tris-HCl(pH 7.7) and heated at 95° C. for 5 minutes on a PCR machine. The temperature is then reduced to 80° C. and slowly decreased at the rate of 0.5° C./minute to final temperature of 42° C. and kept at 42° C. for 2 hours. The DNA is precipitated with ethanol.

Elimination of single-stranded tail

The annealed DNA is suspended in 100 μl of T4 DNA polymerase buffer containing 50 mM Tris-HCl(pH 8.3), 10 mM MgCl$_2$, 1 mM dithiothreitol, 50 mM NaCl, 100 μM each dNTPs. 5 units of T4 DNA polymerase is added and the reaction mixture is incubated at 23° C. for 30 minutes. The reaction is stopped by EDTA at 20 mM (Gubler, *Methods in Enzymology* 152:330, 1987).

Immobilization of the annealed DNA to solid support

75 μg of streptavidin magnetic beads (SIGMA, St. Louis, Mo.) are added to the stopped T4 DNA polymerase reaction and incubated, with shaking, at 23° C. for 20 minutes. The beads are rinsed twice in 0.5 ml 0.5× SSC (Rhoer-Moja et al., *Analytical Biochemistry* 213:12, 1993) and then once in distilled water.

Mismatch-dependent chemical cleavage of the immobilized DNA

All solutions are prepared as described in Saleeba et al., *Methods in Enzymology* 217:286, 1993. For cytosine modification, the magnetic beads with immobilized DNA are suspended in 100 μl of hydroxylamine solution (1.39 g hydroxylamine hydrochloride in 1.6 ml distilled water and 1.75 ml diethylamine, with final pH 6.0), incubated for 30 minutes at 37° C. with shaking, and stopped at 4° C. The magnetic beads are separated from the hydroxylamine solution and rinsed twice with distilled water. The magnetic beads with immobilized DNA are then suspended for thymidine modification in 100 μl of osmium tetroxide solution (0.5 g osmium tetroxide in 12.5 ml distilled water in a glass container), incubated at 37° C. for 3 minutes with shaking, and stopped at 4° C. The osmium tetroxide solution is removed from the magnetic beads. The beads are rinsed twice with distilled water. The dried magnetic beads are suspended in piperidine solution (1:10 diluted in distilled water before use), heated at 90° C. for 30 minutes with shaking. The piperidine solution is separated from the magnetic beads at 90° C. at the end of the incubation. The piperidine solution, which contains cleaved DNA, is frozen and lyophilized. The cleaved DNA is suspended in 30 μl of 50 mM NaCl/10 mM Tris-HCl(pH 8.3)/10 mM MgCl$_2$/1 mM dithiothreitol. 30 μg of fresh streptavidin magnetic beads are added and incubated with shaking at 23° C. for 20 minutes, then removed from the solution and discarded. The DNA is precipitated with ethanol.

Addition of homopolymer tail to the cleaved DNA

The cleaved DNA is suspended in 20 μl of buffer containing 100 mM potassium cacodylate, 30 mM Tris-HCl(pH 7.0), 1 mM CaCl$_2$, 0.1 mM dithiothreitol, 0.1 μM dCTP and 20 units of terminal deoxynucleotidyl transferase (Gibco BRL, Grand Island, N.Y.). The reaction is carried out at 37° C. for 2 minutes followed by phenol-chloroform extraction and ethanol precipitation (Nelson et al., *Methods in Enzymology* 68:41, 1979). The temperature and incubation time for the transferase reaction are empirically determined to ensure formation of homopolymer tail with average length of 15 to 20 nucleotides (Michelson et al., *Journal of Biological Chemistry* 257:14773, 1982).

Formation of double-stranded DNA

The cleaved DNA fragments with homopolymer tail are mostly single-stranded and need to be converted to double-stranded DNA for subsequent cloning. The DNA is suspended in 20 μl of T4 DNA polymerase buffer as described above containing 0.5 μM of poly-dG$_{12-18}$ and 1 unit of T4 DNA polymerase. The reaction mixture is incubated at 23° C. for 30 minutes. The reaction is then stopped by EDTA at 20 mM. The DNA is precipitated with ethanol.

Ligation of linker to blunt-ended DNA

The DNA is suspended in 20 μl of ligation buffer containing 66 mM Tris-HCl(pH 7.6), 5 mM MgCl$_2$, 5 mM dithiothreitol, 0.5 mM ATP. SalI linker 5'-CGGTCGACCG-3' [SEQ ID NO:11] (New England Biolabs, Beverly, Mass..) is added to final concentration of 5 μM, and 2 Weiss units of T4 DNA ligase is added. Incubate the reaction for 16 hours at 16° C. The DNA is precipitated with ethanol and then resuspended in 20 μl of SalI digestion buffer containing 150 mM NaCl, 10 mM Tris-HCl(pH 7.9), 10 mM MgCl$_2$, 1 mM dithiothreitol, 100 μg/ml BSA and 10 units of SalI restriction enzyme. Incubate the reaction at 37° C. for 24 hours. The DNA is precipitated with ethanol.

Cloning and sequencing of the DNA

The DNA is suspended in 10 μl of ligation buffer as described above. 10 ng of SalI digested plasmid vector pGEM -3Zf(+) (Promega) and 2 Weiss units of T4 DNA ligase are added. Incubate the reaction at 16° C. for 16 hours. The ligated DNA is directly transformed into *E.coli* competent cells which are then spread on X-Gal plates. Single-stranded DNAs are made from white colonies selected from the X-Gal plates. The DNAs are sequenced using Sequenase kit and T7 sequencing primer (United States Biochemical, Cleveland, Ohio).

Identifying the mutations

The sequence of the clones are compared with that of chloramphenicol acetyltransferase gene. Considerable number of clones contain a 102 basepair sequence corresponding to the CAT sequence between the PvuII and the altered EcoRI sites. One end of the identified CAT partial sequence is at the altered EcoRI site.

Detecting Sequence Genes with Alternatively Spliced Transcripts

Figure 3:
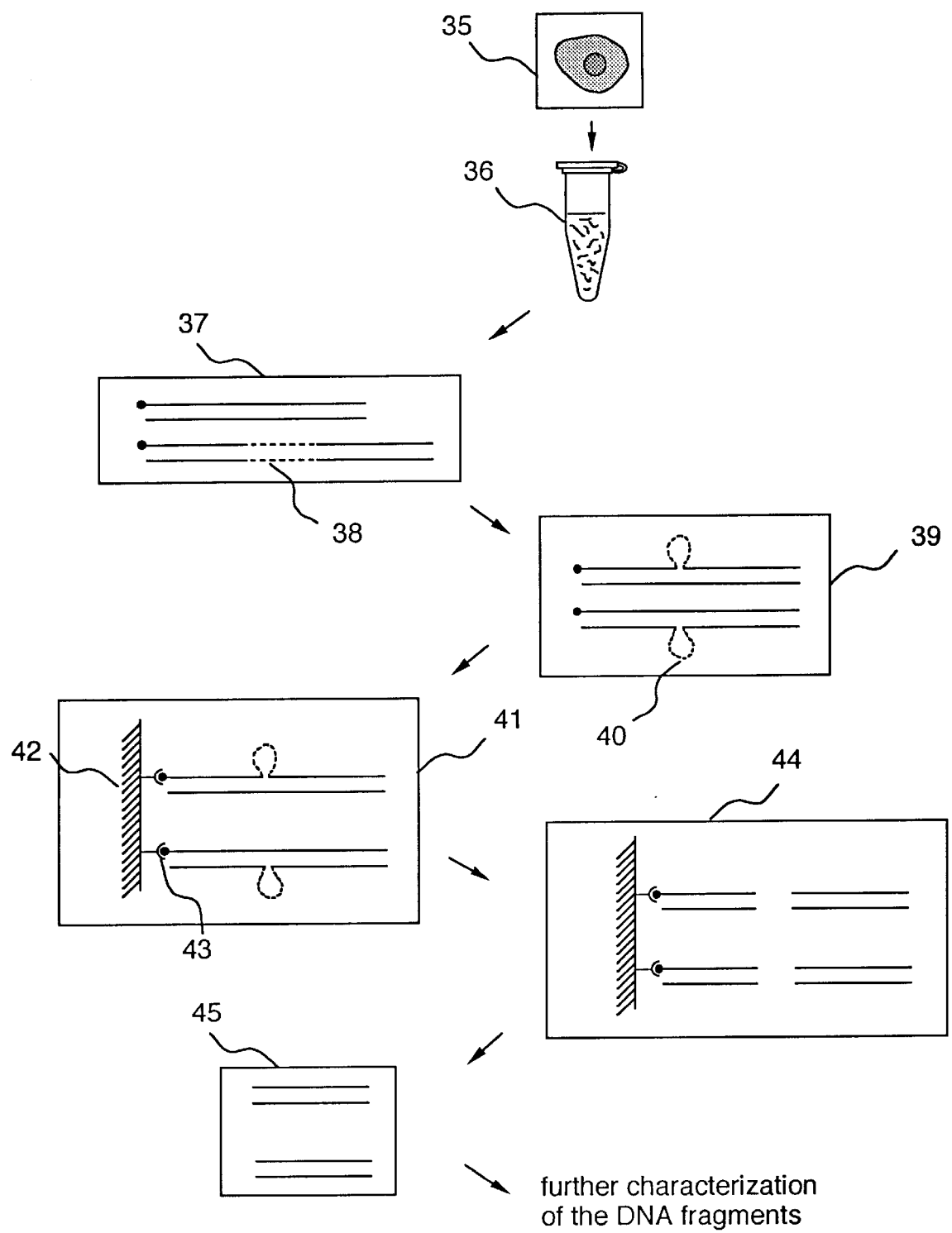
FIG. 3 is a schematic representation of a method according to the present invention for identifying cDNAs that have alternatively spliced sequences.

The techniques of the present invention can be used to identify genes whose transcripts are alternatively spliced. FIG. 3 presents a schematic representation of a method of finding such genes according to the present invention.

Specifically, as shown in FIG. 3, RNA (mRNA or total RNA) is isolated from a single cell 35 according to known procedures (see, for example, Gilman et al. *Current Protocols in Molecular Biology*, Ausubel et al., eds., John Wiley & Sons, N.Y., Chapter 4, 1994; Xie et al., *BioTechniques* 11:324, 1991; Walther et al. *Nuc. Acids Res.* 21:1682, 1993; Aviv et al. *Proc. Natl. Acad. Sci. USA* 69:1408, 1972, each of which is incorporated herein by reference; see also commercial kits available from Pharmacia Biotech, Piscataway, N.J., 1995 catalog #27-9255-01 and #27-9254-01; Stratagene, La Jolla, Calif. 1995 catalog #200347, #200345, #200348, #200349, #200944).

The isolated RNA 36 is converted to double-stranded DNA (dsDNA) through reverse transcription with a biotinylated poly-T primer, followed by second-strand synthesis, as described in the above discussion of FIG. 1. The population of biotinylated dsDNA 37 contains individual duplexes corresponding to individual gene transcripts. Alternative splicing produces transcripts of different lengths from the same gene. Thus, the biotinylated dsDNA 37 contains duplexes of different lengths that correspond to different, alternatively-spliced transcripts of the same gene. For example, FIG. 3 shows dsDNA duplexes corresponding to two alternatively spliced transcripts from the same gene and illustrates that the longer dsDNA duplex contains a region 38 that is not present in the shorter duplex.

The dsDNA population 37 is exposed to denaturing and reannealing conditions as discussed above, so that heteroduplex dsDNAs, whose individual strands are products derived from different individual transcripts from the same gene. As shown in FIG. 3, heteroduplexes formed from strands that correspond to alternatively-spliced transcripts from the same gene have a bulged region 40 of non-complementarity.

The re-annealed dsDNA population 39 is treated so that overhangs are removed or filled in (see above), and duplexes are then immobilized on a solid surface coated with streptavidin 43. The solid-immobilized DNA 41 is cleaved as discussed above, and freed fragments 45 are used to identify the genes whose transcripts were alternatively spliced.

It is noted that, where the present invention is being utilized to compare mRNA samples in order to identify genes with disease-causing mutations (see above), the presence of alternatively-spliced transcripts in the mRNA populations could create background cleavage reactions that would complicate mutation identification. Such interference by alternatively-spliced RNAs can be reduced if each nucleic acid sample to be compared is first denatured, reannealed, and cleaved, preferably without being immobilized on the solid surface, before being mixed with any other nucleic acid sample. This treatment destroys heteroduplexes resulting from hybridization of strands corresponding to different, alternatively-spliced transcripts from the same gene before the individual nucleic acid samples are compared to one another, and therefore maximizes the chance that mismatch-containing heteroduplexes produced during the comparison represent interesting sequence alterations. Each time the denaturation-renaturation-cleavage cycle is repeated, the number of bulged duplexes resulting from alternative splicing is reduced by half. We note that this treatment is not necessarily universally desirable, as the induction of an alternative splicing pathway may, in some cases, be the disease-causing sequence alteration of interest.

OTHER EMBODIMENTS

The present invention has been described above with reference to certain preferred embodiments. Modifications and alterations to the above-described procedures that do not depart from the spirit or scope of the present invention will be apparent to those of ordinary skill of the art and are intended to be encompassed within the following claims.

I claim:

1. A method of identifying a gene whose nucleotide sequence is altered in different cells without knowing in advance which genes have altered sequences in the different cells, the method comprising steps of:

providing a first nucleic acid population from a first cell in which the gene has a first nucleotide sequence;

providing a second nucleic acid population from a second cell in which the gene has a second nucleotide sequence that differs from the first nucleotide sequence in that at least one nucleotide has been substituted, added, deleted, or rearranged;

forming heteroduplexes between nucleic acid strands in the first and second nucleic acid populations, at least one of the heteroduplexes having a mismatch due to the at least one difference in nucleotide sequence;

cleaving the at least one mismatched heteroduplex in a mismatch-dependent manner; and isolating at least one cleavage product; and using the at least one isolated cleavage product to identify the gene whose nucleotide sequence was altered in the second cell as compared with the first cell.

2. The method of claim 1, further including steps of:

immobilizing the mismatch-containing heteroduplexes on a solid phase; and exposing the solid phase to a solution phase, wherein the step of isolating cleavage products comprises:
    releasing the cleavage products into the solution phase; and
    separating the solution phase containing the cleavage products from the solid phase.

3. A method of identifying a gene whose transcript is alternatively spliced without prior knowledge of the gene sequence, the method comprising steps of:

providing an RNA sample from a cell;

producing a double-stranded DNA population from the RNA;

exposing the double-stranded DNA population to denaturing conditions;

exposing the denatured DNA to annealing conditions so that heteroduplex double-stranded DNAs are formed, at least one heteroduplex double-stranded DNA consisting of a first strand corresponding to a first alternatively spliced transcript of a gene and a second strand corresponding to a second alternatively spliced transcript of the same gene, the at least one heteroduplex double-stranded DNA containing an unpaired region;

cleaving the at least one heteroduplex containing an unpaired region at the unpaired region;

isolating at least one cleavage product; and using the at least one isolated cleavage product to identify the gene whose transcript was alternatively spliced.

4. The method of claim 3, further including a step of immobilizing the heteroduplex double-stranded DNA on a solid phase, wherein the step of isolating cleavage products comprises separating from the solid phase cleavage products present in a solution phase.

* * * * *